United States Patent [19]

Popil et al.

[11] Patent Number: 5,278,411
[45] Date of Patent: Jan. 11, 1994

[54] RESIDUAL INK MEASUREMENT

[75] Inventors: Roman Ewhen Popil, White Rock; Kevin C. D. Houston, New Westminister, both of Canada

[73] Assignee: MacMillan Bloedel Limited, Vancouver, Canada

[21] Appl. No.: 955,170

[22] Filed: Oct. 1, 1992

[51] Int. Cl.⁵ ............................................. G01N 21/88
[52] U.S. Cl. .................. 250/330; 250/358.1; 250/341; 250/360.1; 162/263
[58] Field of Search ................... 250/341, 358.1, 359.1, 250/360.1, 330; 162/263

[56] References Cited

U.S. PATENT DOCUMENTS

| | | | |
|---|---|---|---|
| 4,931,657 | 6/1990 | Houston et al. | 250/559 |
| 4,935,628 | 6/1990 | Martin et al. | 250/351 |
| 4,964,949 | 10/1990 | Hamaguchi et al. | 162/5 |

OTHER PUBLICATIONS

"On-line Automated Pulp Dirt Count Measurement", Kenesy et al., TAPPI Proceedings Pulping Conference 1987.

Primary Examiner—Carolyn E. Fields
Attorney, Agent, or Firm—C. A. Rowley

[57] ABSTRACT

A method and apparatus for detecting residual ink in a sample by illuminating by diffused infra-red light a series of spots on a sample and examining a small area on each spot by collecting light in a video camera to form a frame for each spot, digitizing each of the frame and detecting areas in the frames having a brightness below a selected level to determine the total dark area of each frame. The number of such frames processed in a set of frames used to categorize the sample is defined when a certain minimum number of frames have been processed and when a selected degree of convergence of the data collected for the set and the data from the frame currently being processed is obtained, or after a preset maximum number of frames have been processed. The sample is characterised on the basis of the ratio of the dark area to the total area processed.

11 Claims, 3 Drawing Sheets

RESIDUAL INK MEASUREMENT

FIELD OF THE INVENTION

The present invention relates to a dirt counter. More particularly the present invention relates to a residual ink detector for determining the amount of residual ink in a paper sample.

BACKGROUND TO THE INVENTION

The concept of detecting dirt in pulp or counting the number of specks, i.e. areas of different color, based on analyzing a moving web using a charge coupled device (CCD) camera has been used for example in the Intel Dirt Counter TM made by Intel and described in *On-Line Automated Pulp Dirt Count Measurement* by Kenesy et al presented at the TAPPI Proceedings Pulping Conference in 1987. This device scans the pulp surface using a CCD Camera each pixel of which functions as a discrete sensor. The camera is focused onto the pulp surface so that each pixel measured a section of pulp 0.15 mm wide. The surface of the pulp is illuminated from the same side as the camera and the dirt detected is size classified and a dirt count number weighted by particle size and normalized is determined.

U.S. Pat. No. 4,931,657 issued Jun. 5, 1990 to Houston et al also discloses a dirt counter which counts the number of pixels of intensity below a certain level as set by thresholding the signal with acceptance or rejection being based on the total area occupied by dirt particles or by the inclusion of significant large areas of single dirt spots.

It is also common practice to inspect the pulp visually and determine the quality of pulp subjectively and to base acceptance or rejection of the pulp for cleanliness on the subjective judgement of the inspector.

None of these techniques for detecting dirt are adequate or capable of defining the residual ink in recycled paper products.

BRIEF DESCRIPTION OF THE PRESENT INVENTION

It is an object of the present invention to provide a method and apparatus for detecting residual ink in a paper sheet made from recycled fibres.

Broadly the present invention relates to a method and apparatus for detecting residual ink in a sample comprising illuminating means for directing diffused infra-red light to illuminate a spot on said sample, a video camera means having lens means for collecting light reflecting from a portion of said spot and directing it to said camera means to define a frame, means for relatively moving said sample to said illuminating means and said camera between frames of a set so that each frame represents a different portion of said sample, computer means having means for digitizing each of said frames of video, means for detecting dark areas with a brightness below a selected level in each said frame, means for processing at least a first preselected minimum number of said frames and means for defining the number of frames in said set to provide a representative sample based on a preselected degree convergence of data collected for said set with data from said frame currently being processed or after a preselected maximum number of frames of said set of frames have been processed and means for characterizing said sample based on determining at least one of the average dark area per unit area of said frames of said set processed and the average number of said dark areas detected per frame in said set.

Preferably said preselected degree of convergence comprises determining the frame contain the largest dark area found on processed of said frames of a set of frames, and said frame containing the largest dark area causing less than a preselected percentage change in the average dark area per frame.

Preferably the resolution of the optical system will be better than 10 microns, preferably between 2 and 5 microns.

Preferably said computer means counts the number of dark areas in each frame and the size of such dark areas and provides a continuous histogram with the number of different sized dark areas detected to provide an indicated of the number of areas and their sizes.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

Figure 1:
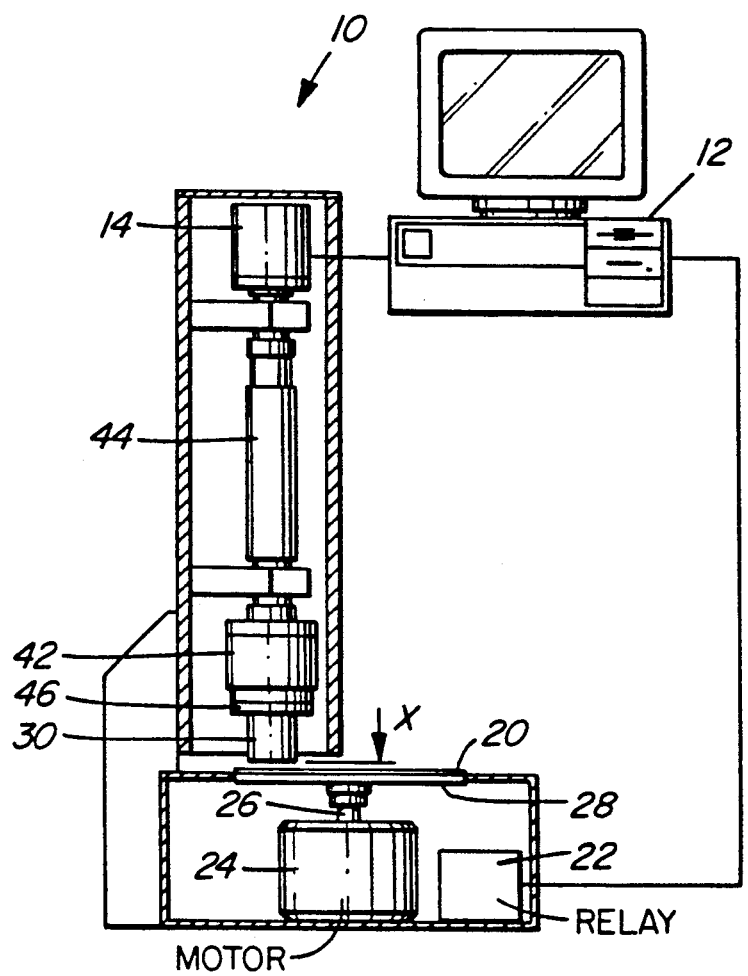
FIG. 1 is a schematic illustration of the residual ink measurement of the device of the present invention.

The sensor 10 of the present invention includes a computer 12 fitted with a digitizer board that receives a signal from a video camera 14 which in turn receives light from a portion or an zone 16 of an illuminated spot 18 on a sample 20 (see FIG. 3) to generate a video image. The computer 12 via a relay 22 controls the drive motor 24 which drives a shaft 26 and a disk 28 upon which the sample 20 is mounted.

Figure 3:
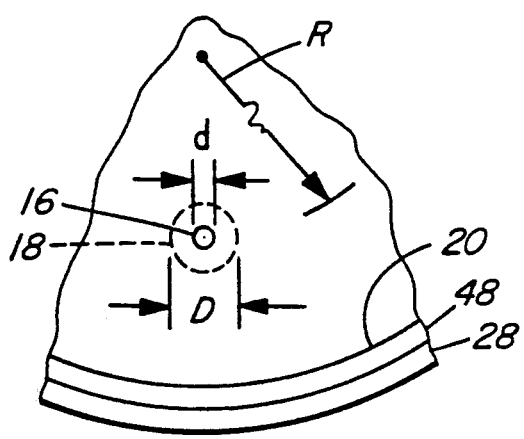
FIG. 3 is a view looking parallel to the focal axis of the video camera showing an spot of the sample onto which diffused light is projected.
Figure 2:
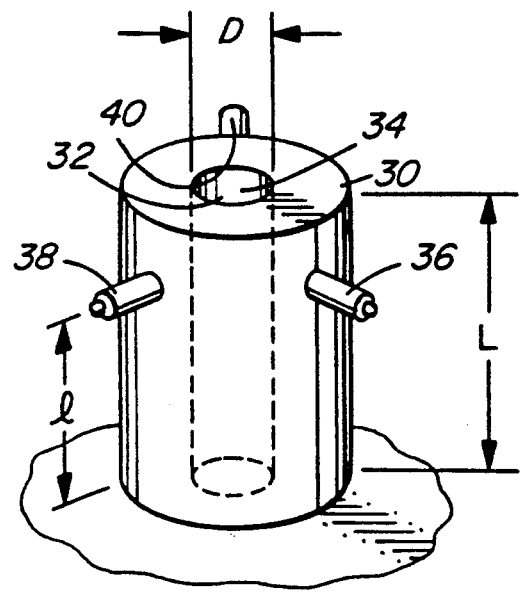
FIG. 2 is an isometric illustration of a suitable diffuse light source that may be used with the present invention.

The spot 18 is illuminated on the sample via diffusing light source 30 (see FIGS. 1 and 2) which is provided with a central longitudinal passage 32 of a diameter D = to about 1 centimeter, generally in the order of about 0.5 to 1.5 centimeters and is provided on its inner surface 34 with a substantially flat white face 34. Three light sources 36, 38 and 40 spaced from the end 31 through which light is directed onto the sample 20 a distance to ensure the light from the sources 36, 38 and 40 enters the passage 32 and is reflected back and forth across the passage 32 a sufficient number of times to diffuse the light. These light sources 36, 38 and 40 are arranged symmetrically about the passage 32, i.e. arranged at 120° to each other circumferentially to the passage 32 in a plane perpendicular to the axis of the passage. This diffused light is projected onto the sample 20 to illuminate the spot 18 as shown in FIG. 3. It is important to use diffused light due to the position of the residual ink spots on and in the paper. If properly diffused light is not used to illuminate the spot, the sensor 10 is not effective.

The diffusing light source 30 will have a length L compatible with the focal length of the lens being used (i.e. generally about 2–4 cm) and the light of the light of the lights 36, 38 and 40 indicated by letter l will normally be about l/L=about 0.75.

The light sources 36, 38 and 40 provide a source of infra-red light (e.g. a tungsten filament bulb) so that the spot 18 is illuminated by a significant amount of infra-red light. The use of infra-red light is important to the effectiveness of the invention as such light does not penetrate the paper in the same manner as other types of light and is essential to providing a signal that may effectively be used to determine the residual ink.

The lens system 42 which directs light through the extension of 44 to the camera 14 is focused on the zone 16 within the spot 18. The zone 16 is significantly smaller than the area 18 and generally will have an equivalent diameter d of 0.5 to 1.5 millimeters, preferably 1 millimeter, i.e. about 1/10 the diameter of spot 18. The lens system 42 uses an auto-iris lens to ensure the light reading the camera is substantially constant, i.e. the average signal level from the camera is held substantially constant.

An infra-red cut-on filter 46 filters the light entering the lens system 42 so that the camera 14 is subjected primarily to light in the infra-red spectrum.

The sample 20 is mounted on the disk 28 which is provided with a background surface 48 that is substantially white so that substantially all of the light reflected block through the sample 20 (see FIG. 3).

Figure 4:
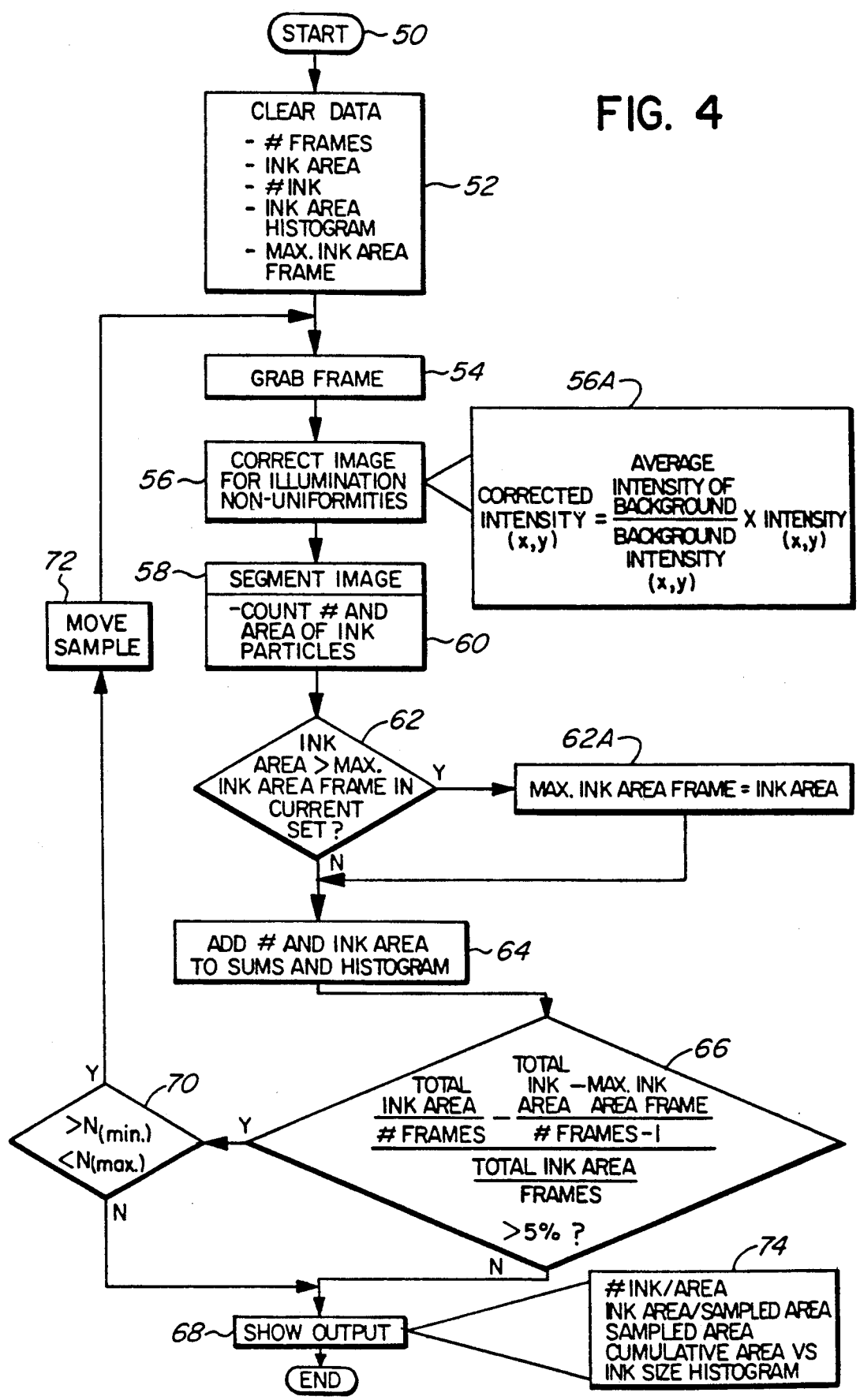
FIG. 4 is a flow diagram of the operation system of the present invention.

The operation of the system will be evident from FIG. 4.

As shown the operation commences at start 50 and clears the data from the system as indicated at 52 making the system ready for operation on the next set of frames. The first operation is a frame grab where the video camera takes as a frame the portion or zone 16 within the illuminated area 18 as indicated at 54. This frame or image is then digitized and processed.

The first step in processing each image of the set is, as indicated at 56, to correct the image for illumination non-uniformities. This is accomplished by using a previously acquired background image (based on the average of several images of ink free samples, e.g. samples of virgin pulp) which has the brightness of the type of samples being process and applying the following correction factor $$I_{c(x,y)} = \frac{I_{BA} \times I_{(x,y)}}{I_{B(x,y)}} \quad (1)$$

where
$I_{c(x,y)}$ = corrected intensity for the pixel being processed
$I_{BA}$ = average intensity for the background
$I_{B(x,y)}$ = background image intensity for the pixel being processed
$I_{(x,y,)}$ = the measured intensity for the pixel being processed.

In other words, the Corrected Intensity ($I_{c(x,y)}$) for the pixel is equal to the average intensity for the background image multiplied by the measured intensity for that pixel divided by the background intensity for that pixel and these corrected values are used to form a corrected image as indicated at 56.

The corrected image is then segmented at indicated at 58 and then the number of particles (areas of brightness below a selected value) counted and the area of the particles recorded. Particles less than a predetermined size need not be counted. Particles less than approximately 4 pixels for the order of magnitude of the area represented by the frame being processed (i.e. wherein 1 millimeter is viewed by approximately 500 pixels or each pixel represents an area of 4 square microns) were not counted.

The ink area (particle area) is then compared, as indicated at 62, with the maximum ink area found in a frame of the frames forming part of the current set and if the ink area of the current frame is larger, the ink area measured for the current frame becomes the maximum ink area frame for the next frames in the set of frames being analyzed as indicated at 62A.

Next, the number of particles by ink area for the frame being processed is added to the sums previously accumulated in processing the current set of frames to accumulate a histogram as indicated at 64.

It is important to know when to terminate the test. This requires that at least a certain minimum number of frames of data be processed [$N_{(min)}$] and less than a certain maximum cutoff number [$N_{(max)}$] so that the number of frames processed in any given set exceed the minimum and are equal to or less than the maximum. It is desirable to keep the number of frames to a minimum and still obtain a meaningful evaluation thus a system for determining whether or not a meaningful number of frames have been processed is employed after the preselected $N_{(min)}$ frames have been processed. These systems rely on convergence of the data for the then being processed frames with the data from the frames of the set that have already been processed.

Convergence of the data can be measured in a number of different ways, for example by a kernel method, wherein the data in a set kernel size is compared with the total accumulated data to see that it is within a certain range or percentage of the total accumulated data. The preferred system, as will described herein below, also accommodates a discrete frame found during the processing that has the largest darkened area, i.e. the highest residual ink content per frame.

In practising the preferred method, the accumulated data for the set of frames being processed and the data for the last frame processed are then subjected to the analysis as indicated at 66 to determine if the set is complete by applying the following formula.

$$\frac{T/N - (T - M)/(N - 1)}{T/N} = R \quad (2)$$

where
T = total ink area for all frames processed
N = number of frames processed for the set of frames
M = dark area of the maximum ink area frame for the set being processed
R = result When R is greater than a preselected number (P) selected depending on the accuracy desired (0.05, i.e. 5% has been found adequate but 3 to 10% depending on the processing time available may be used) the relay 22 is triggered to advance the sample 20 to view a new zone 16 and grab a new frame, i.e. if R>P sample 20 advanced and a new frame grabbed.

When the number of frames processed (N) in the set is less than a preselected minimum number of frames $N_{(min)}$ have been processed, i.e. $N<N_{(min)}$ a preselected number ($N_{(min)}$ 50 has been found satisfactory but any reasonable number, generally between 10 and 150 could be chosen) the decision is always made as indicated at 70 to trigger the relay 22 as indicated at 72 regardless of the value of R.

After the preselected minimum number of frames $N_{(min)}$ have been processed and if R is less than the preselected number P (i.e., R<P), the set of frames is deemed complete and no further frames are processed for that set.

After the minimum $N_{(min)}$ frames have been processed and a preselected maximum number of frames $N_{(max)}$ are processed without R being less than P (R<P) as indicated at 66 the set of frames is also deemed completed and no further frames are processed even though R is still greater than P (R>P).

$N_{(max)}$ is set based on time constraints and limitation on sample size and normally will not exceed 500, more preferably 300. For the purposes of the present invention the $N_{(max)}$ was set at 200.

The above described system of determining a representative sample as digitized in stages 62, 62A and 66 may be substituted with other means for defining when there is sufficient convergence of the data to justify terminating the set.

The output 68 may be shown in a variety of different ways as indicated at 74. For example, a histogram of the number of ink spots of a preselected area such as that shown in FIG. 5 may be plotted on an accumulated basis until the criteria of 66 and/or 70 are met, i.e. R<P and $N>N_{min}$ or $N=N_{(max)}$.

Figure 5:
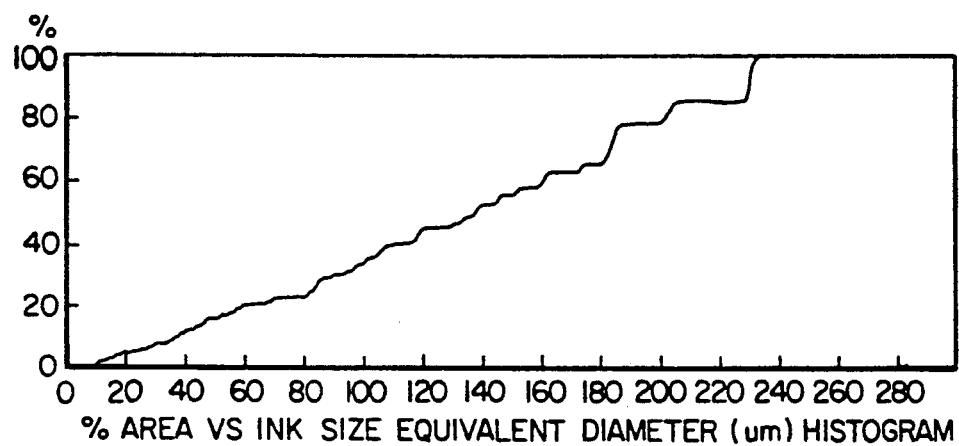
FIG. 5 is a histogram of percent area versus ink size equivalent diameter generated by the present invention by analyzing a sample.

One may also simply show the number of ink spots per unit area or the ratio of ink area to total sample area or the total accumulated area versus ink size histogram as above described with respect to FIG. 5.

Figure 6:
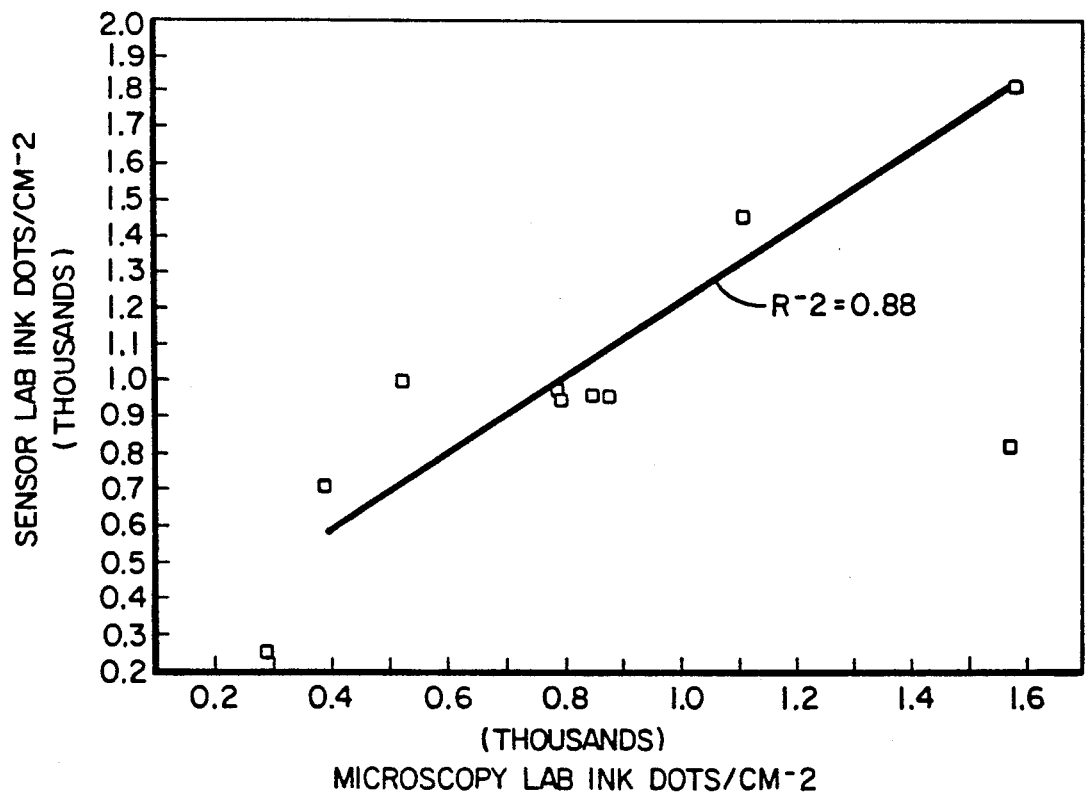
FIG. 6 is a view of a graph similar to FIG. 6 but based on a number of ink dots found.

FIG. 6 shows a comparison of results obtained using the present invention compared with the results obtained by analyzing the same sample under accepted standard laboratory conditions using a microscopic image analysis. The points plotted are the ratio dirt area to total area processed for the sample (dirt area for the set of frame/total area of the set of frames). The results for various tests have been indicated by sample numbers 1 to 10 inclusive (each test represents the analysis of a set of frames).

It can be seen in FIG. 6 the present invention correlates well with the laboratory assessment.

Having described the invention modifications will be evident to those skilled in the art without departing from the spirit of the invention as defined in the appended claims.

We claim:

1. An apparatus for detecting residual ink in a sample comprising illuminating means for providing a source of infra-red light, means for diffusing said infra-red light and for directing diffused infra-red light to illuminate a spot on said sample, a video camera means having lens means for collecting said light reflecting from a portion of said spot and directing it to said camera means to define a frame of video information, means for moving said sample relative to said means for diffusing and said camera means between frames in a set of frames so that each frame in said set represents a different portion of said sample, computer means having means for digitizing each of said frames, means for detecting dark areas with a brightness below a selected level in each said frame, means for processing at least a first preselected minimum number of said frames and continuing to process frames in said set until a selected degree of convergence of data collected for said set of frames and data from said frame currently being processed is attained, but terminating processing if a a preselected maximum number of frames of said set of frames have been processed and said selected degree of convergence of data collected has not been attained thereby to define a representative number of frames in said set and means for characterizing said sample based on determining at least one of the average dark area per unit area of said frames of said set of frames processed and the average number of said dark areas detected per frame in said set.

2. An apparatus as defined in claim 1 wherein said means for moving includes a support surface for said sample and said support surface has a substantially flat white face.

3. An apparatus as defined in claim 1 wherein said computer means further includes means to count the number of dark areas in each frame and register the size of such dark areas and provide a histogram of the number of dark areas of different sizes detected to provide an indication of the number of areas and their sizes.

4. An apparatus as defined in claim 3 wherein said means for moving includes a support surface for said sample and said support surface has a substantially flat white face.

5. A method for detecting residual ink in a sample comprising diffusing light from an infra-red light source and directing diffused infra-red light to illuminate a spot on said sample, collecting light reflecting from a portion of said spot and directing said light reflecting from said portion of said spot to a video camera to define a frame of video information of a set of frames, digitizing said frame of video information from said camera, detecting dark areas with a brightness below a selected level in each said frame of said set, relatively moving said sample and said light source together with said camera between each said frame of said set, processing at least a first preselected number of said frames and thereafter continuing to process said frames until a selected degree of convergence of the data collected for the set and the data from the frame currently being processed, but terminating said processing if a preselected maximum number of frames of said set of frames have been processed and said selected degree of convergence of data collected as not being attained thereby to define the number of frames in said set and characterizing said sample based on determining at least one of the average dark area per unit area of said frames of said set and the number of said dark areas detected in said set.

6. A method as defined in claim 5 wherein the resolution of said portion in said frame has a maximum dimension of no more than 10 microns.

7. A method as defined in claim 6 further comprising correcting said frame for illumination non-uniformity before processing by applying the correcting factor $$I_{c(x,y)} = \frac{I_{A(i)} \times I_{(x,y)(i)}}{I_{B(x,y)}} \quad (1)$$

where
$I_{c(x,y)}$ = corrected intensity for the pixel being processed
$I_{A(i)}$ = average intensity for the frame being processed
$I_{B(x,y)}$ = background intensity for the pixel being processed $I_{(x,y),(i)}$ = the measured intensity for the pixel being processed.

8. A method as defined in claim 6 wherein said maximum dimension is in the range of between 2 and 5 microns.

9. A method as defined in claim 5 wherein said determining comprises counting a number of dark areas in each frame and the size of such dark areas and provides a continuous histogram of the number of different sizes of dark areas detected to provide an indication of the number of dark areas and their size.

10. A method as defined in claim 9 further comprising correcting said frame for illumination non-uniformity before processing by applying the correcting factor $$I_{c(x,y)} = \frac{I_{A(i)} \times I_{(x,y)(i)}}{I_{B(x,y)}} \quad (1)$$

where $I_{c(x,y)}$ = corrected intensity for the pixel being processed $I_{A(i)}$ = average intensity for the frame being processed $I_{B(x,y)}$ = background intensity for the pixel being processed $I_{(x,y),(i)}$ = the measured intensity for the pixel being processed.

11. A method as defined in claim 5 further comprising correcting said frame for illumination non-uniformity before processing by applying the correcting factor $$I_{c(x,y)} = \frac{I_{A(i)} \times I_{(x,y)(i)}}{I_{B(x,y)}} \quad (1)$$

where $I_{c(x,y)}$ = corrected intensity for the pixel being processed $I_{A(i)}$ = average intensity for the frame being processed $I_{B(x,y)}$ = background intensity for the pixel being processed $I_{(x,y),(i)}$ = the measured intensity for the pixel being processed.

* * * * *